United States Patent
Nosé et al.

(10) Patent No.: US 7,686,758 B2
(45) Date of Patent: Mar. 30, 2010

(54) CANNULA TIP FOR A CARDIAC ASSIST DEVICE

(75) Inventors: Yukihiko Nosé, Houston, TX (US);
Toshiyuki Shinohara, Saitama (JP);
Kuniyoshi Watanabe, Nagano (JP);
Tadashi Motomura, Houston, TX (US)

(73) Assignees: HITMAC (USA), Inc., Houston, TX (US); Baylor College of Medicine, Houston, TX (US)

( * ) Notice: Subject to any disclaimer, the term of this patent is extended or adjusted under 35 U.S.C. 154(b) by 687 days.

(21) Appl. No.: 11/527,097

(22) Filed: Sep. 25, 2006

(65) Prior Publication Data

US 2007/0049787 A1    Mar. 1, 2007

Related U.S. Application Data

(63) Continuation-in-part of application No. 10/655,489, filed on Sep. 3, 2003, now abandoned.

(60) Provisional application No. 60/409,885, filed on Sep. 10, 2002.

(51) Int. Cl.
*A61N 1/372*    (2006.01)
(52) U.S. Cl. ........................................ 600/16
(58) Field of Classification Search ............... 600/16; 606/181, 185
See application file for complete search history.

(56) References Cited

U.S. PATENT DOCUMENTS

| | | | |
|---|---|---|---|
| 2,201,749 A | 5/1940 | Vandegrift | |
| 4,639,252 A | 1/1987 | Kelly et al. | |
| 4,680,029 A | 7/1987 | Ranford et al. | |
| 4,863,441 A | 9/1989 | Lindsay et al. | |
| 5,061,256 A | 10/1991 | Wampler | |
| 5,906,824 A | 5/1999 | Suzuki et al. | |
| 6,007,478 A | 12/1999 | Siess et al. | |
| 6,712,797 B1 | 3/2004 | Southern, Jr. | |
| 2002/0082467 A1* | 6/2002 | Campbell | 600/16 |
| 2004/0054377 A1 | 3/2004 | Foster et al. | |

OTHER PUBLICATIONS

Undated photograph "Range of Cannulas," printed from the Press Center Section of Berlin Heart AG's web site www.berlinheart.com (one page).

G. Xu et al., "Oxygen ion implantation at 20 to 2000 keV into polysulfone for improvement of endothelial cell adhesion," Elsevier Science B.V., Colloids and Surfaces B: Biointerfaces 19 (2000) pp. 237-247.

(Continued)

*Primary Examiner*—Carl H Layno
*Assistant Examiner*—Rex Holmes
(74) *Attorney, Agent, or Firm*—Lipsitz & McAllister, LLC

(57) ABSTRACT

The present invention provides an inflow cannula tip that is shaped to prevent suction with the ventricular wall and adapted to prevent platelet adhesion. In particular, the inlet portion of the cannula tip comprises two projections extending from the cylindrical body of the cannula tip with gaps between the projections. The projections may have beveled edges. The inlet portion of the cannula tip can accept blood flow from either the gaps in the side or from the bottom of the tip. Even if the edge of the cannula tip is close to or even touching ventricle wall, a suction condition will not result, as blood is allowed to flow through the gaps between the projections.

22 Claims, 5 Drawing Sheets

OTHER PUBLICATIONS

M. Kaibara et al., "Proliferation of endothelial cells on the plasma-treated segmented-polyurethane surface: attempt of construction of a small caliber hybrid vascular graft and antithrombogenicity," Elsevier Science B.V., Colloids and Surfaces B: Biointerfaces 19 (2000) pp. 209-217.

K. Kurotobi et al., "Ion implantation into collagen-coated surfaces for the development of small diameter artificial grafts," Elsevier Science B.V., Colloids and Surfaces B: Biointerfaces 19 (2000) pp. 227-235.

* cited by examiner

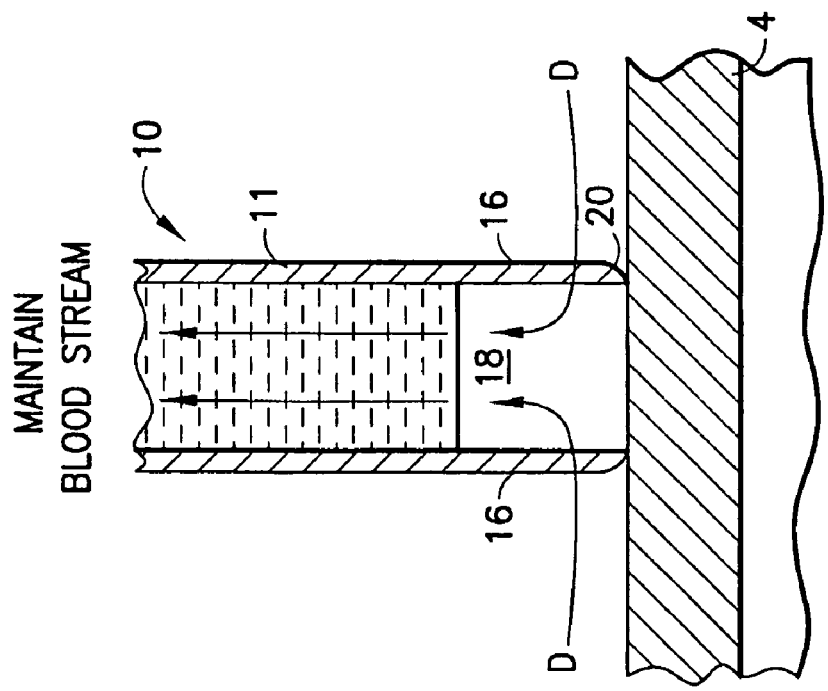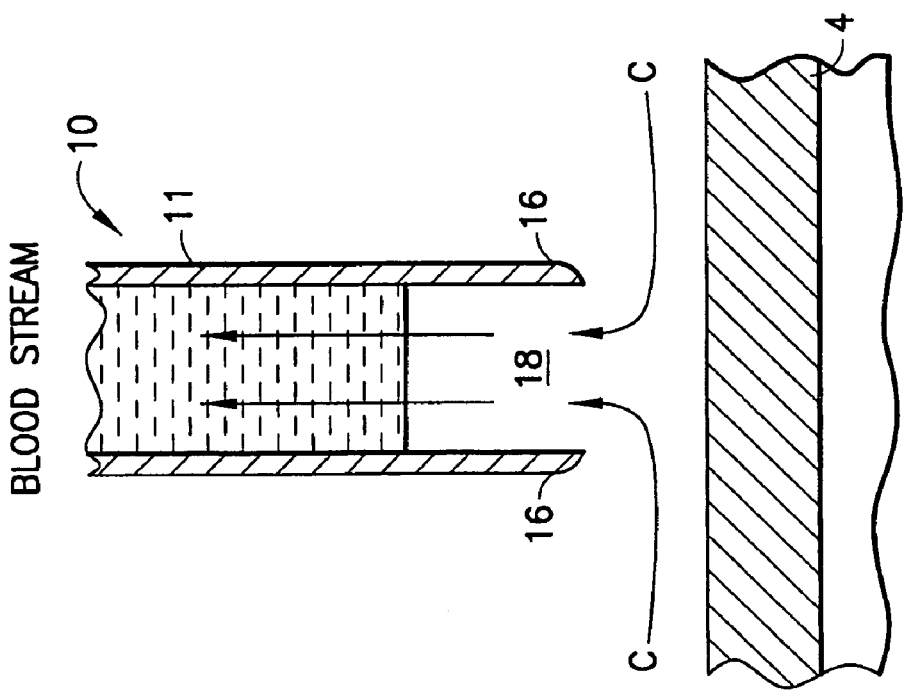

CANNULA TIP FOR A CARDIAC ASSIST DEVICE

This application is a continuation-in-part of U.S. patent application Ser. No. 10/655,489 filed on Sep. 3, 2003, which claims the benefit of U.S. provisional patent application No. 60/409,885 filed on Sep. 10, 2002, which is incorporated herein and made a part hereof by reference.

BACKGROUND OF THE INVENTION

The present invention relates to the field of cardiac assist devices, such as blood pumps and the like. More specifically, the present invention relates to a cannula tip for use at the inflow of a blood pump that is designed to avoid the creation of a suction condition.

Bypass type cardiac assist devices are used frequently in advanced stages of heart failure to assist the failing human heart. It is typical for such devices to be used as left ventricular assist devices (LVAS) or right ventricular assist devices (RVAS).

Approximately 30% of the deaths of LVAS patients are the result of excessive venous pressure, increase in the hepatic portal vein pressure, and multi-organ failure. Over 60,000 patients a year who experience heart failure will require cardiac assist devices.

One problem associated with an implanted cardiac assist device is decreased pump flow volume which may result when the inflow cannula tip becomes attached to the ventricle wall resulting in a "suction condition". In addition to decreasing the pump flow volume, such a suction condition will also limit the output of the natural heart, leading to sudden decrease in blood pressure, blood circulatory failure, and possible death.

The suction condition is more prevalent with a right ventricular assist pump. The inflow conduit of a right ventricular assist pump is inserted directly through the right ventricular wall near the pulmonary arterial valve. Anatomically there is not enough space available at this location between the right ventricular wall and the septum. Thus, a suction condition will occur easily unless a proper inflow tip is provided.

This suction condition may be caused by improper positioning of the cannula tip, excessive pump flow volume, outside pressure of the heart, etc. It is imperative to prevent the occurrence of such a suction condition.

A further problem associated with implantable cardiac assist devices is platelet adhesion on the inflow cannula tip, leading to the clots which reduce and ultimately prohibit blood flow.

It would be advantageous to provide a cannula tip for use at the pump inflow which is shaped to avoid the occurrence of the suction condition. It would also be advantageous to provide an inflow cannula tip that is resistant to platelet adhesion and the formation of blood clots.

The inflow cannula tip of the present invention provides the foregoing and other advantages.

SUMMARY OF THE INVENTION

The present invention relates to a cannula tip for the inflow of a blood pump that is designed to prevent the occurrence of a suction condition. The inventive inflow cannula tip is particularly useful for a right ventricular assist device. The inventive inflow cannula tip may also be used with a left ventricular assist device.

In accordance with one example embodiment of the invention, an inflow cannula tip for use with a cardiac assist device is provided. The cannula tip has a hollow cylindrical body with a first end adapted for connection to a cannula for an implantable cardiac assist device. The cannula tip also has an open-ended inlet portion at a second end of the body comprising two unconnected projections extending from the cylindrical body and forming two gaps between the projections. A ratio of a diameter of the inlet portion to the depth of the gaps may be in a range of between approximately 1.5-3.5.

In one example embodiment, the diameter of the inflow portion may be approximately 0.625 inches and the depth of the gaps may be approximately 0.31 inches. Such an embodiment of a cannula tip may be particularly advantageous for use with a long term implantable left ventricular assist device.

In a further example embodiment, the two gaps may comprise a proximal gap and a distal gap. The distal gap may have a smaller depth than the proximal gap. For example, the diameter of the inflow portion in such an embodiment may be approximately 0.625 inches, while the depth of the proximal gap may be approximately 0.31 inches and the depth of the distal gap may be approximately 0.21 inches. Such an embodiment of a cannula tip may be particularly advantageous for use with a long term implantable right ventricular assist device.

In another example embodiment, the projections may comprise semi-circular projections. The projections may have beveled edges. The gaps may be approximately U-shaped gaps.

The cannula tip may be integrally formed with the cannula. Alternatively, the cannula tip may be formed as a separate piece that may be connected to the cannula.

The cannula tip may comprise one of a biocompatible hard plastic, a biocompatible carbon material, and a biocompatible metal. For example, the cannula tip may comprise one of polyvinyl or polyurethane. Alternatively, the cannula tip may comprise a titanium alloy. In an embodiment where the cannula tip is comprised of titanium alloy, the cannula tip may be adapted for use with one of a long term implantable left ventricular assist device or a long term implantable right ventricular assist device. The titanium alloy acts to prevent the formation of blood clots on the inlet portion.

In order to prevent platelet adhesion and prevent the formation of blood clots, the cannula tip may be coated with one of crosslinked protein, a biodegradable polymer containing at least one of an anti-platelet, anti-thrombotic, and anti-coagulant drug, and a non-degradable polymer containing at least one of an anti-platelet, anti-thrombotic, and anti-coagulant drug.

Alternatively, the cannula tip may be subjected to a treatment comprising a biocompatible surface modification, such as treatment with an ion beam.

The cannula tip may be adapted for use with one of a pulsatile assist device or a non-pulsatile assist device.

In a further example embodiment of the present invention, an inflow cannula tip for use with a cardiac assist device is provided. The cannula tip has a hollow cylindrical body having a first end adapted for connection to a cannula for an implantable cardiac assist device. The cannula tip also has an open-ended inlet portion at a second end of the body comprising two unconnected projections extending from the body and forming two gaps between the projections. The two gaps comprise a proximal gap and a distal gap, with the distal gap having a smaller depth than the proximal gap.

A ratio of a diameter of the inlet portion to the depth of the gaps may be in a range of between approximately 1.5-3.5. For example, the diameter of the inflow portion may be approximately 0.625 inches, while the depth of the proximal gap may be approximately 0.31 inches and the depth of the distal gap may be approximately 0.21 inches. Such an embodiment of a cannula tip may be adapted for use with a long term implantable right ventricular assist device.

BRIEF DESCRIPTION OF THE DRAWINGS

The present invention will hereinafter be described in conjunction with the appended drawing figures, wherein like reference numerals denote like elements, and:

FIG. 4 (FIGS. 4A and 4B) shows the operation of an example embodiment of the inventive cannula tip;

DETAILED DESCRIPTION

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing an embodiment of the invention. It should be understood that various changes may be made in the function and arrangement of elements without departing from the spirit and scope of the invention as set forth in the appended claims.

The present invention relates to a cannula tip for long term use at the inflow of an implantable blood pump that is designed to prevent the occurrence of a suction condition and the adhesion of platelets. Particular example embodiments of the inventive inflow cannula tip are useful for a right ventricular assist device. Embodiments of the inventive inflow cannula tip may also be used with a left ventricular assist device.

Figure 1B:
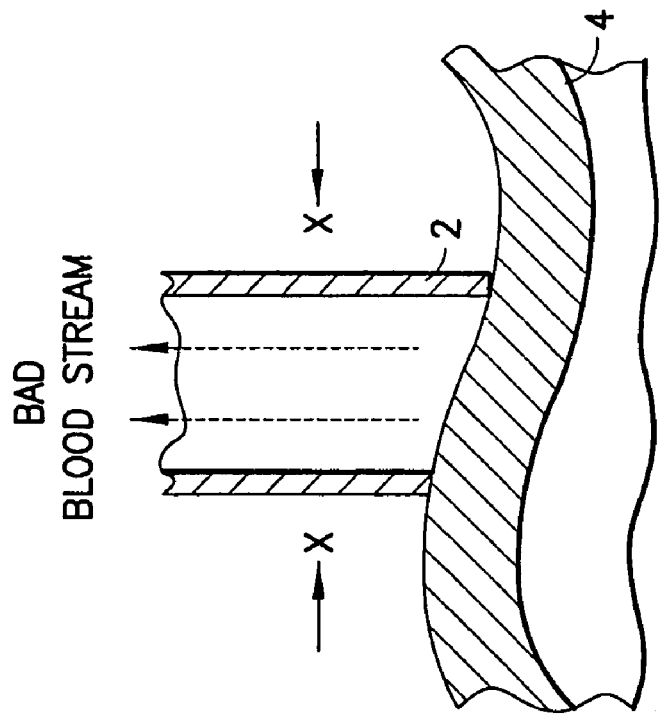
FIG. 1 (FIGS. 1A and 1B) shows the operation of a prior art cannula tip.
Figure 1A:
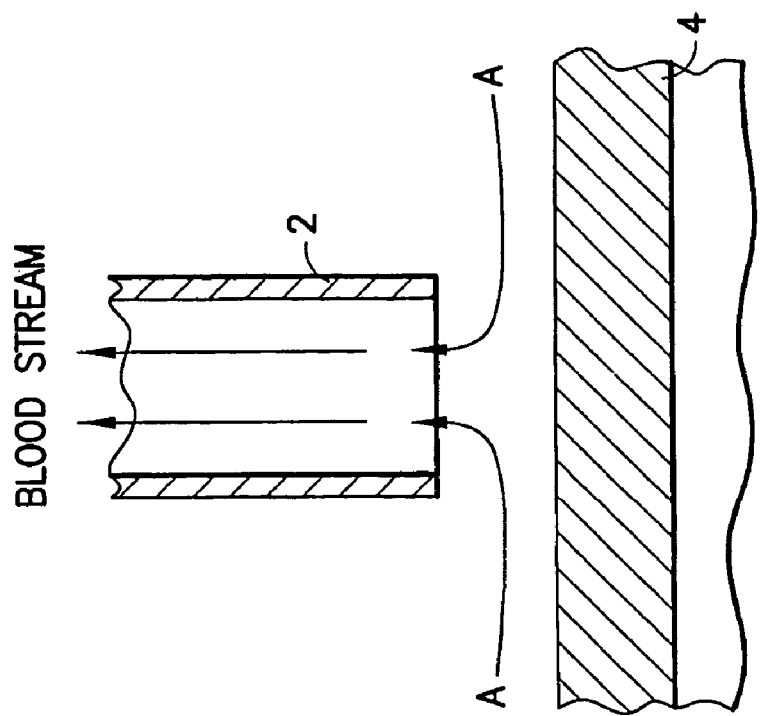

FIGS. 1A and 1B show a prior art cannula tip 2 in operation. This prior art tip 2 is in the form of a cylindrical tube. FIG. 1A shows the prior art cannula tip 2 in normal operation with blood flow in the direction of arrows A. However, the cylindrical tube design of the prior art cannula tip 2 leads to a suction condition with the ventricular wall 4 as shown in FIG. 1B. Such a suction condition hinders blood flow. This suction condition may be caused by improper positioning of the cannula tip, excessive pump flow volume, outside pressure of the heart, or a combination thereof.

With such a cylindrical structure of the prior art cannula tip 2, it is difficult to recover from the suction condition. Attempts have been made to solve this problem in the prior art. For example, prior art cannula tips having a cylindrical structure may be provided with multiple holes in the side of the cylinder. Such a design acts to prevent the suction condition. However, the holes of such a prior art design have a tendency to become occluded by platelet adhesion and blood clots during long-term implantation. The cannula tip of the present invention not only prevents the suction condition, but also prevents platelet adhesion and the formulation of blood clots.

Figure 2:
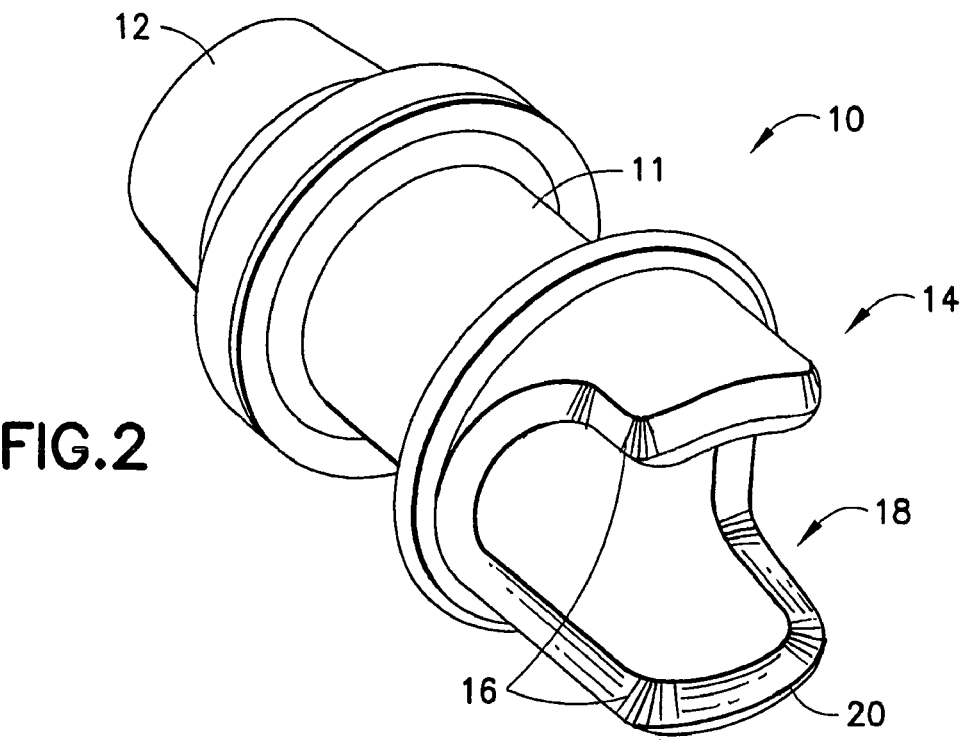
FIG. 2 shows a perspective view of an example embodiment of the inventive cannula tip.
Figure 3:
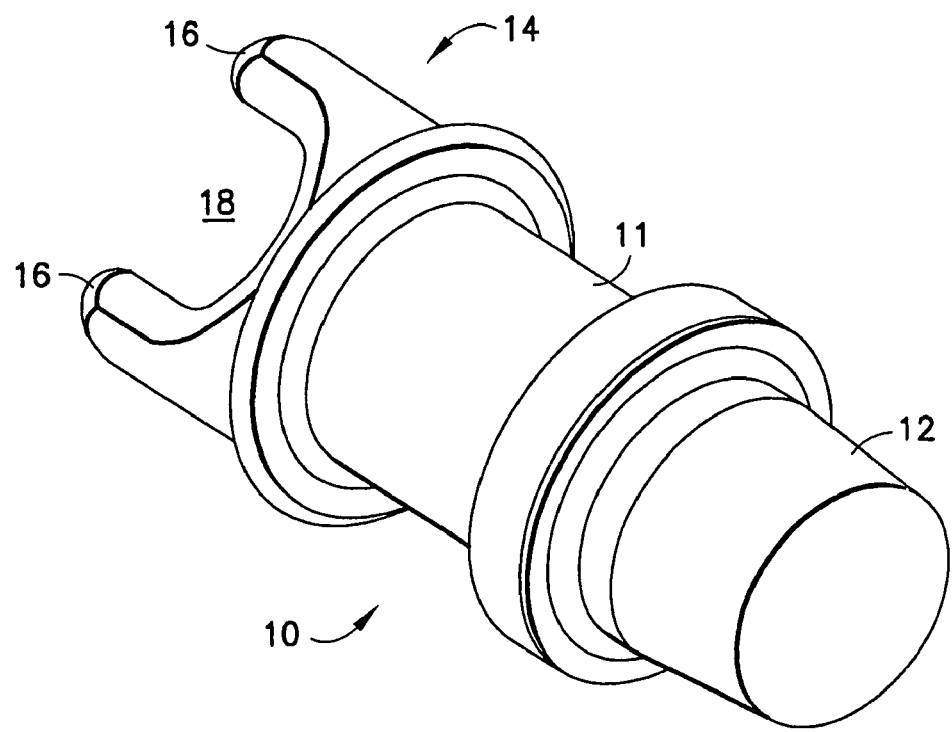
FIG. 3 shows a further perspective view of an example embodiment of the inventive cannula tip.

The mouth (inlet) of the cannula tip of the present invention is shaped to prevent suction when in contact with the ventricular wall. Perspective views of an example embodiment of the present invention are shown in FIGS. 2 and 3. The inventive cannula tip 10 has a hollow cylindrical body 11 with a first end 12 adapted for connection to a cannula for an implantable cardiac assist device (not shown). An open-ended hollow inlet portion 14 of the cannula tip 10 may comprise two unconnected projections 16 extending from the cylindrical body 11 of the cannula tip 10 which projections 16 are positioned so as to provide gaps 18 in the side of the inlet portion 14.

The projections 16 may be in the form of semi-circular projections. The gaps 18 may be generally U-shaped gaps in the inlet portion 14 of the cannula tip 10. The projections 16 may have beveled edges 20. The shape and form of the gaps helps to prevent platelet adhesion and blood clot formation by allowing for improved blood flow as compared to cannula tips having sharp edges and/or hard angles in their design.

The inlet portion 14 of the tip 10 can accept blood flow from either the side or the bottom of the cannula tip as shown in FIGS. 4A and 4B. FIG. 4A shows the operation of the cannula tip 10 of the present invention in a normal operating condition (i.e., not in contact with the ventricle wall 4). In FIG. 4A, blood flow may enter the cannula tip 10 from the bottom as shown by arrows C. As shown in FIG. 4B, if the projections 16 of the cannula tip 10 of the present invention should come in contact with the ventricle wall 4, no suction condition will result, since blood flow may still enter the inlet portion of the cannula tip 10 through the gaps 18 between the projections 16, as shown by arrows D.

Figure 5:
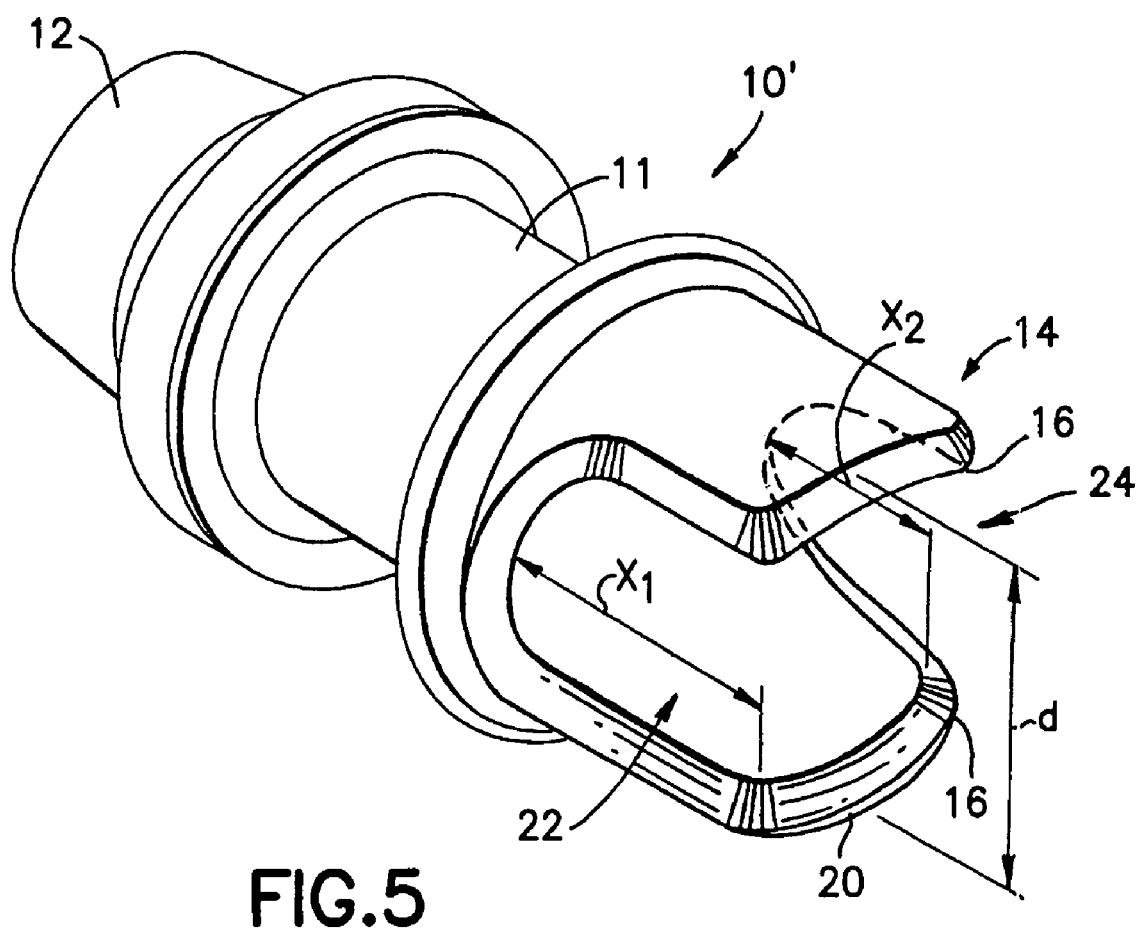
FIG. 5 shows a perspective view of a further example embodiment of the inventive cannula tip.

A further example embodiment of an inflow cannula tip 10' in accordance with the present invention is shown in FIG. 5. The cannula tip 10' has a hollow cylindrical body 11 with a first end 12 adapted for connection to a cannula for an implantable cardiac assist device (not shown). The cannula tip 10' also has an open-ended inlet portion 14 at a second end of the body 11 comprising two unconnected projections 16 extending from the body 11 and forming two gaps 22, 24 between the projections 16.

A ratio of a diameter d of the inlet portion 14 to a depth $X_1$, $X_2$ of the gaps 22, 24 may be in a range of between approximately 1.5-3.5. For example, the diameter d of the inflow portion 14 may be approximately 0.625 inches and the depth $X_1$, $X_2$ of the gaps 22, 24 may be approximately 0.31 inches. Such an embodiment of a cannula tip 10' may be particularly advantageous for use with a long term implantable left ventricular assist device. When used with a left ventricular assist device, depth of the gaps 22, 24 may be adapted to prevent occlusion of the cannula tip 10' (which may result in a suction condition) during left ventricular contraction and/or to prevent contact with the papillary muscle of the mitral valve.

In a further example embodiment, the two gaps 22, 24 may comprise a proximal gap 22 and a distal gap 24. The distal gap 24 may have a smaller depth $X_2$ than the depth $X_1$ of the proximal gap 22. For example, the diameter d of the inflow portion 14 in such an embodiment may be approximately 0.625 inches, while the depth $X_1$ of the proximal gap 22 may be approximately 0.31 inches and the depth $X_2$ of the distal gap 24 may be approximately 0.21 inches. Such an embodiment of a cannula tip 10' may be particularly advantageous for use with a long term implantable right ventricular assist device.

The cannula tip 10' may comprise one of a biocompatible hard plastic, a biocompatible carbon material, and a biocompatible metal. For example, the cannula tip 10' may comprise one of polyvinyl or polyurethane. Alternatively, the cannula tip 10' may comprise a titanium alloy. An embodiment where the cannula tip 10' is comprised of titanium alloy, the cannula tip 10' may be adapted for use with one of a long term implantable left ventricular assist device or a long term implantable right ventricular assist device. The titanium alloy acts to prevent platelet adhesion and the formation of blood clots on the inlet portion 14 of the cannula tip 10'.

In order to prevent platelet adhesion and prevent the formation of blood clots, the cannula tip 10' may be coated with one of crosslinked protein, a biodegradable polymer containing at least one of an anti-platelet, anti-thrombotic, and anti-coagulant drug, and a non-degradable polymer containing at least one of an anti-platelet, anti-thrombotic, and anti-coagulant drug.

Alternatively, the cannula tip 10' may be subjected to a treatment comprising a biocompatible surface modification, such as treatment with an ion beam. Ion beam treatments for increasing endothelial cell adhesion and reducing platelet adhesion are known in the art and are described in, for example, U.S. Pat. No. 5,906,824 to Suzuki, et al.

Figure 6:
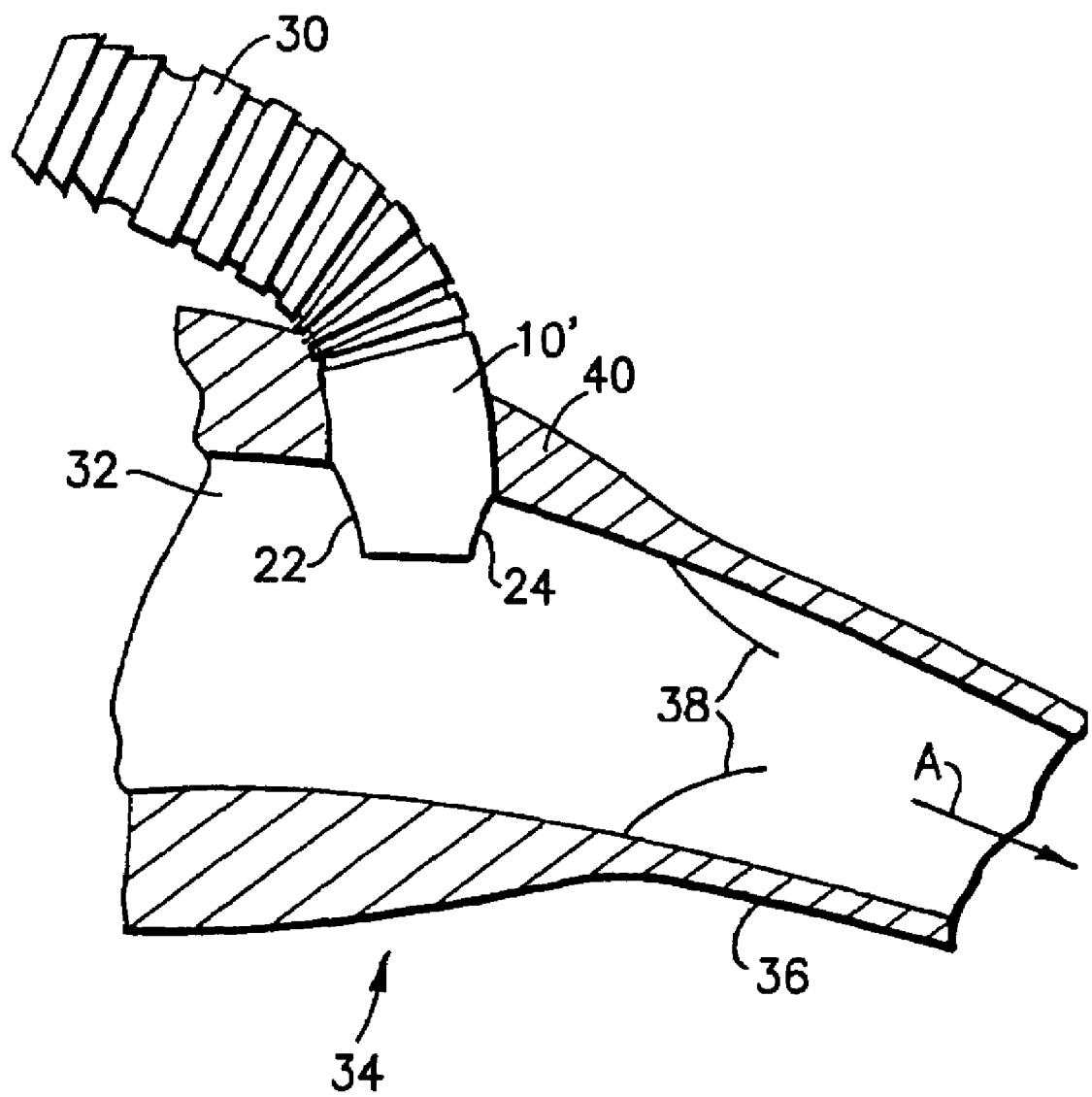
FIG. 6 shows the cannula tip of FIG. 5 positioned in a right ventricular outflow track.

FIG. 6 shows the cannula tip 10' of FIG. 5 attached to a cannula 30 of an implantable cardiac assist device. The cannula tip 10' is shown positioned (implanted) in the infundibulum 32 of the right ventricular outflow tract 34 close to the pulmonary artery 36. Arrow A shows the direction of blood flow through the pulmonary artery 36 from the heart to the lungs through the pulmonary valve 38. In particular, the cannula tip 10' is positioned in the infundibulum 32 just below the pulmonary valve 38 and angled to provide the best anatomical fit between the anterior wall of the right ventricle and the posterior sternal wall, which is a narrow space. For a better fit, the cannula tip 10' and/or the cannula 30 to which it is attached, may be curved as shown in FIG. 6.

As discussed above in connection with FIG. 5, in such an example embodiment as shown in FIG. 6, the depth of the proximal gap 22 may be larger than the depth of the distal gap 24. It is advantageous if the distal gap 24, which is closest to the pulmonary valve 38, has a smaller depth than the proximal gap 22, in order to prevent extension of the distal gap 24 into the right ventricular free wall 40. This prevents the possibility of trauma to the ventricular wall 40 and/or blood leakage into the chest cavity.

Those skilled in the art will appreciate that, although the figures show two projections 16 extending from the cannula tip body 11, more than two projections extending from the body 11 of the cannula tip 10, 10' may be provided having gaps between the projections. Also, it should be appreciated that the cannula tip 10, 10' may comprise various other shapes which will similarly prevent a suction condition by allowing blood flow even when the tip is close to or touching the ventricular wall.

The tip 10, 10' may be a separate piece that can be connected to a cannula. Alternatively, the tip 10, 10' may be formed together with a cannula as a single piece.

The cannula tip 10, 10' of the present invention does not require complex structure and design. Further, the inventive tip 10, 10' does not interfere with the insertion of the cannula into the ventricle.

The cannula tip 10, 10' can be used for both pulsatile heart assist devices and non-pulsatile heart assist devices. The cannula tip 10, 10' may also be successfully used in other applications where the insertion of a cannula is required.

It should now be appreciated that the present invention provides an advantageous inflow cannula tip that prevents the formation of a suction condition and prevents platelet adhesion and the formation of blood clots.

Although the invention has been described in connection with various illustrated embodiments, numerous modifications and adaptations may be made thereto without departing from the spirit and scope of the invention as set forth in the claims.

What is claimed is:

1. An inflow cannula tip for use with a cardiac assist device, comprising:
    a hollow cylindrical body having a first end adapted for connection to a cannula for an implantable cardiac assist device; and
    an open-ended inlet portion at a second end of said body comprising two projections extending from said body and forming two gaps between said projections, the gaps being designed and adapted to prevent a suction condition when said cannula tip is in an implanted position and the open-ended inlet portion is in contact with an inner wall surface of an organ;
    wherein:
    the cannula tip is comprised of a hard material; and
    a ratio of a diameter of the inlet portion to the depth of the gaps is in a range of between approximately 1.5-3.5.

2. An inflow cannula tip in accordance with claim 1, wherein:
    the diameter of the inflow portion is approximately 0.625 inches; and
    the depth of the gaps is approximately 0.31 inches.

3. An inflow cannula tip in accordance with claim 2, wherein the cannula tip is for use with a long term implantable left ventricular assist device.

4. An inflow cannula tip in accordance with claim 1, wherein:
    the two gaps comprise a proximal gap and a distal gap;
    said distal gap has a smaller depth than said proximal gap.

5. An inflow cannula tip in accordance with claim 1, wherein:
    the diameter of the inflow portion is approximately 0.625 inches;
    the depth of the proximal gap is approximately 0.31 inches; and
    the depth of the distal gap is approximately 0.21 inches.

6. An inflow cannula tip in accordance with claim 5, wherein the cannula tip is for use with a long term implantable right ventricular assist device.

7. An inflow cannula tip in accordance with claim 1, wherein said projections comprise semi-circular projections.

8. An inflow cannula tip in accordance with claim 1, wherein said gaps are approximately U-shaped gaps.

9. An inflow cannula tip in accordance with claim 1, wherein said projections have beveled edges.

10. An inflow cannula tip in accordance with claim 1, wherein said cannula tip is integrally formed with said cannula.

11. An inflow cannula tip in accordance with claim 1, wherein said hard material comprises one of a biocompatible hard plastic, a biocompatible carbon material, and a biocompatible metal.

12. An inflow cannula tip in accordance with claim 11, wherein said cannula tip comprises one of polyvinyl or polyurethane.

13. An inflow cannula tip in accordance with claim 11, wherein said cannula tip comprises a titanium alloy.

14. An inflow cannula tip in accordance with claim 13, wherein said cannula tip is adapted for use with one of a long term implantable left ventricular assist device or a long term implantable right ventricular assist device.

15. An inflow cannula tip in accordance with claim 13, wherein said titanium alloy acts to prevent the formation of blood clots on said inlet portion.

16. An inflow cannula tip in accordance with claim 1, wherein said cannula tip is coated with one of crosslinked proteins, a biodegradable polymer containing at least one of an anti-platelet, anti-thrombotic, and anti-coagulant drug, and a non-degradable polymer containing at least one of an anti-platelet, anti-thrombotic, and anti-coagulant drug.

17. An inflow cannula tip in accordance with claim 1, wherein:
    said cannula tip is subjected to a treatment comprising a biocompatible surface modification.

18. An inflow cannula tip in accordance with claim 1, wherein said cannula tip is adapted for use with one of a pulsatile assist device or a non-pulsatile assist device.

19. An inflow cannula tip for use with a cardiac assist device, comprising:
    a hollow cylindrical body having a first end adapted for connection to a cannula for an implantable cardiac assist device; and
    an open-ended inlet portion at a second end of said body comprising two projections extending from said body and forming two gaps between said projections, the gaps being designed and adapted to prevent a suction condition when said cannula tip is in an implanted position and the open-ended inlet portion is in contact with an inner wall surface of an organ;
    wherein:
    the cannula tip is comprised of a hard material; and
    said two gaps comprise a proximal gap and a distal gap, said distal gap having a smaller depth than said proximal gap.

20. An inflow cannula tip in accordance with claim 19, wherein a ratio of a diameter of the inlet portion to the depth of the gaps is in a range of between approximately 1.5-3.5.

21. An inflow cannula tip in accordance with claim 19, wherein:
    the diameter of the inflow portion is approximately 0.625 inches;
    the depth of the proximal gap is approximately 0.31 inches; and
    the depth of the distal gap is approximately 0.21 inches.

22. An inflow cannula tip in accordance with claim 19, wherein said cannula tip is adapted for use with a long term implantable right ventricular assist device.

* * * * *